Oct. 7,1975 R.S. MOORE Plant Pat. 3,792
MINATURE ROSE PLANT
Filed August 23,1974
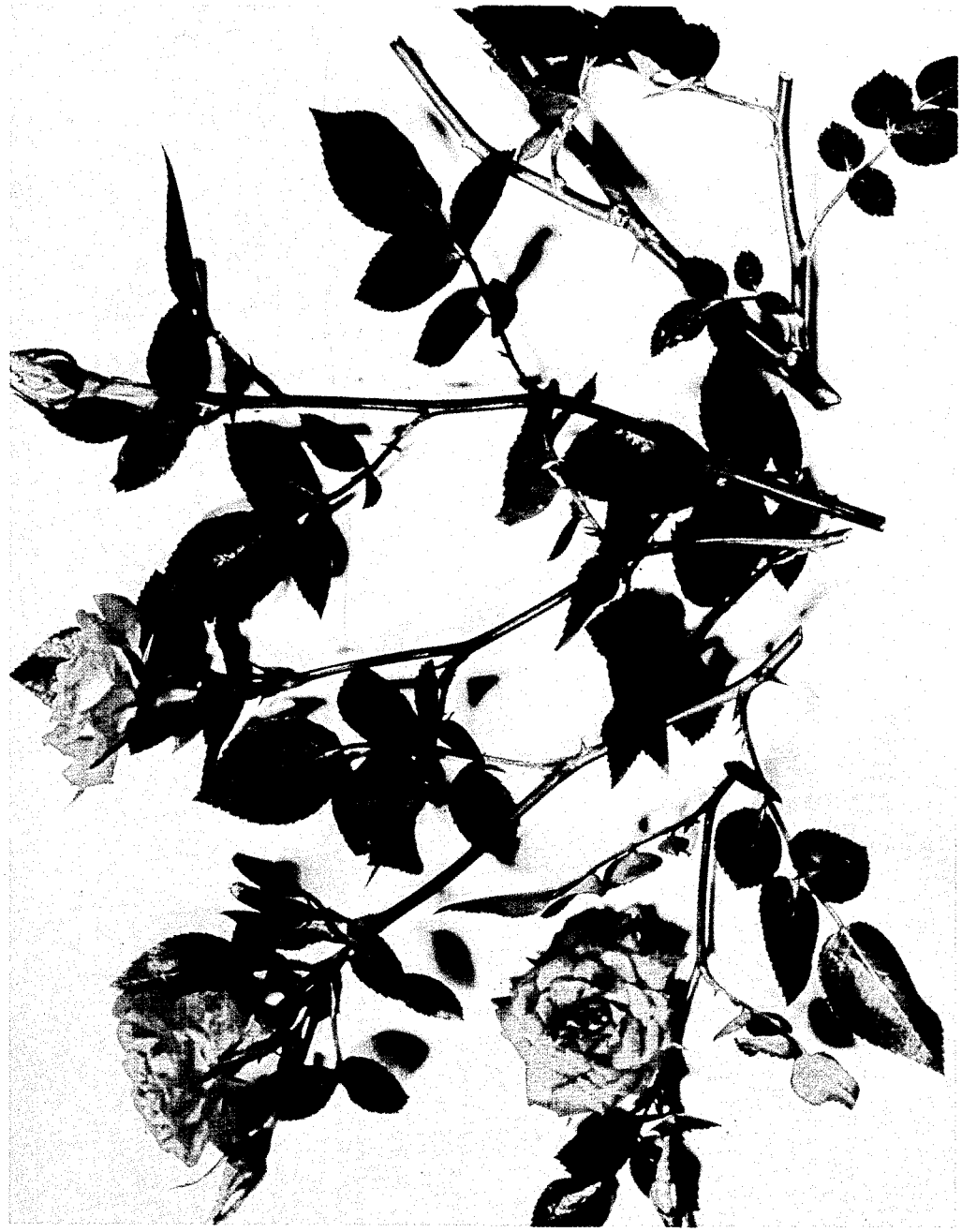

United States Patent

Plant Pat. 3,792

Patented Oct. 7, 1975

3,792

MINIATURE ROSE PLANT

Ralph S. Moore, Visalia, Calif., assignor of a fractional part interest to Ernest D. Williams, Dallas, Tex.

Filed Aug. 23, 1974, Ser. No. 500,195

Int. Cl. A01h *5/00*

U.S. Cl. Plt.—7 1 Claim

The present invention relates to a new and distinct variety of hardy, dwarf, bush type rose plant of the miniature class; the variety being primarily characterized—as to novelty—by buds and flowers of deep pink color with reverse (back side) of petals of lighter intensity.

The variety is further characterized by:

An abundance of bloom, with flowers borne singly or several to the stem in loose clusters or sprays.

Little or no fragrance.

A plant which is vigorous, of rounded spreading shape and with semi-glossy, moderately small foliage with pointed leaflets; the flowers and foliage being similar in size to the variety "Janna" (United States Plant Pat. No. 3,245). The plant, which has a normal height of 14 to 16 inches can easily be maintained at 12 inches or less by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between "Little Darling" (floribunda—Plant Pat. No. 1,581, expired) as the seed parent and an unnamed variety [(Rosa Wichuraina × Floradora) × (Oakington Ruby × Floradora)] all unpatented kinds, as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed Type: Hardy; dwarf; bush; seedling; greenhouse; outdoors; cut flowers; garden decoration; potted plant.

Class: Miniature.

Flowers:

*Continuity.*—Continuous; repeat bloom all season.

*Fragrance.*—Light, sweet.

Flowers borne: Singly and several together (3 to 5) on strong, medium length stems.

Quantity of bloom: Abundant both outside and in greenhouse.

Bud:

*Peduncle.*—Medium length; sturdy; erect; medium green, sometimes tinted bronze; with numerous very small short hairs. Before calyx breaks; size—small. Form medium long; pointed; with foliaceous appendages and numerous tiny short hairs on surface of bud; with foliaceous parts extending beyond the tip of the bud equal to one-half or more of its length. Color—medium green, often tinted with bronze. As calyx breaks, color—dark pink to dark red. As first petal opens: dark pink to red with near white to greenish area at base—size—small.

*Bloom.*—Size when fully open—small, averaging about 3–3.5 cm. (1¼"). Petalage—very double—70 to 80 (plus several narrow petaloids) arranged regularly. Form—high centered with petals rolled loosely outward, and later at maturity rounded with high center with petals rolled loosely outward and downward.

*Petals.*—Fairly thick; satiny both inside and outside. Shape—Outside petals, broad lanceolate with wedge shaped base and acute tip; intermediate—broad lanceolate with acute tip; inside—lanceolate with acute tip.

*Color.*—Newly opened flower from a plant grown outdoors August 1974, Visalia, Calif. Outside petal: Outside surface—white or near white, overlaid near tip with Rose Madder 23/2 and gradually blending to white in the lower one-half or more of petal; inside surface—white or near white overlaid near tip with Rose Bengal 25, and blending into white on basal one half of petal. Intermediate petal: Outside surface—white or near white with some color from inside surface bleeding through on upper ½ of petal surface; inside surface—white or near white overlaid with Rose Bengal 25 and blending into white on lower one half of petal. Inner petal: Outside surface—white or near white with color from inside surface bleeding through near tip portion of petal; inside surface—essentially same as intermediate petal. General color effect newly opened flowers—deep pink color; Three days open—deep pink. Behavior—as flowers age petals usually become darker shade before dropping off. Spent petals drop off (may hang on in cool damp weather). Flower longevity (August 1974)—bush in garden or pot 4 to 5 days or longer. Cut flowers at living room temperature 3 to 4 days or longer.

Reproductive organs:

*Stamens.*—None.

*Filaments.*—None.

*Pollens.*—None.

*Pistils.*—All malformed (not functional).

*Styles.*—Uneven; medium to short; bunched greenish.

*Stigma.*—Missing.

*Ovaries.*—All enclosed in calyx.

*Hips.*—None.

*Sepals.*—Permanent; spear shaped.

*Seeds.*—None.

Foliage:

*Leaves.*—Compound of five leaflets, sometimes three; abundant; small to moderately small; leathery, semi-glossy.

*Leaflets.*—Shape: broad lanceolate; apex acute; base acute or rounded acute. Margin serrate. Color: normal green; new growth sometimes lightly tinted bronze. Rachis: medium strength; upper side smooth except for few very tiny prickles, grooved; underside sparsely thorny with few or no prickles. Stipules: fairly long; medium width; medium length narrow points which turn out at about 45 degrees.

Growth:

*Habit.*—Dwarf; bushy; rounded; much branched.

*Growth.*—Free; vigorous.

*Canes.*—Medium; slender.

*Main stems.*—Color: dull green. Thorns: few, medium length, hooked (curved) slightly downward; color: brown. Prickles—none. Hairs—none.

*Branches.*—Color: medium green. Thorns: sparsely thorny; medium length; hooked downward. Medium to short oval base; color: brown. Prickles—none. Hairs—none.

*New Shoots.*—Color: medium green, often tinted bronze.

*Thorns.*—Few to moderate; medium length; hooked downward. Reddish to brown color; sharp points; base oval. Prickles—none.

*Hairs.*—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of minature rose plant of hardy, dwarf, rounded, much branched, bush type, as illustrated and described, characterized by buds and flowers resembling the "Janna" (Plant Pat. 2,450) miniature rose in general form and size, the color being a deep pink and the individual petals having considerable near white area at base on both upper and lower surfaces; the general color effect being pink; and further characterized by a plant which is of vigorous and relatively compact growth, easy to propagate from cuttings, with moderately small, leathery, semi-glossy foliage; an abundance of bloom, with flowers borne singly or several to stem in loose cluster.

No references cited.

ROBERT E. BAGWILL, Primary Examiner